(12) United States Patent
Kho et al.

(10) Patent No.: US 9,474,509 B2
(45) Date of Patent: Oct. 25, 2016

(54) APPARATUS AND METHOD FOR GENERATING ULTRASONIC IMAGE

(71) Applicant: SAMSUNG ELECTRONICS CO., LTD., Suwon-si (KR)

(72) Inventors: Young-Ihn Kho, Seoul (KR); Hee-Sae Lee, Yongin-si (KR); Min-Su Ahn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 250 days.

(21) Appl. No.: 13/940,805

(22) Filed: Jul. 12, 2013

(65) Prior Publication Data
US 2014/0073925 A1     Mar. 13, 2014

(30) Foreign Application Priority Data
Sep. 12, 2012   (KR) .......................... 10-2012-0100886

(51) Int. Cl.
*A61B 8/00*   (2006.01)
*A61B 8/08*   (2006.01)

(52) U.S. Cl.
CPC ............. *A61B 8/483* (2013.01); *A61B 8/0866* (2013.01); *A61B 8/466* (2013.01); *A61B 8/5207* (2013.01); *A61B 8/56* (2013.01)

(58) Field of Classification Search
CPC .... A61B 8/0866; A61B 8/466; A61B 8/483; A61B 8/5207; A61B 8/46; A61B 8/12; A61B 8/463; A61B 8/06; G01S 7/52071
USPC ........................... 600/437–469; 382/128–132
See application file for complete search history.

(56) References Cited

U.S. PATENT DOCUMENTS

| | | | | |
|---|---|---|---|---|
| 6,254,540 | B1* | 7/2001 | Kikuchi et al. ............... | 600/443 |
| 8,519,998 | B2* | 8/2013 | Hashimoto et al. .......... | 345/424 |
| 2005/0203417 | A1* | 9/2005 | Okuno .......................... | 600/463 |
| 2006/0112033 | A1* | 5/2006 | Vion et al. ..................... | 706/16 |
| 2006/0184028 | A1* | 8/2006 | Wen .............................. | 600/441 |
| 2006/0241428 | A1* | 10/2006 | Kao .............................. | 600/437 |
| 2007/0014446 | A1* | 1/2007 | Sumanaweera et al. ..... | 382/128 |
| 2007/0167754 | A1* | 7/2007 | Okuno et al. ................. | 600/437 |
| 2009/0124907 | A1* | 5/2009 | Bruce et al. .................. | 600/458 |
| 2010/0022880 | A1* | 1/2010 | Sathyanarayana et al. .. | 600/443 |
| 2010/0056924 | A1* | 3/2010 | Powers ......................... | 600/458 |
| 2011/0162673 | A1* | 7/2011 | Samain et al. ................ | 132/317 |

(Continued)

FOREIGN PATENT DOCUMENTS

| KR | 2002-0012419 A | 2/2002 |
|---|---|---|
| KR | 10-2010-0040557 A | 4/2010 |

(Continued)

*Primary Examiner* — Sanjay Cattungal
(74) *Attorney, Agent, or Firm* — Sughrue Mion, PLLC

(57) ABSTRACT

An apparatus for generating a 3D ultrasonic color image of a fetus based on skin color of a mother includes a sample image acquisition unit acquiring a sample image by photographing a skin of a pregnant woman, a 2D color map generator generating a 2D color map based on the sample image, a probe irradiating ultrasonic signals into the pregnant woman and receiving reflected ultrasonic echo signals, a volume data generator generating 3D volume data based on the ultrasonic echo signals, and a controller generating a 3D ultrasonic color image of the fetus by applying values of the 2D color map to a 3D ultrasonic image obtained by volume rendering of the 3D volume data.

22 Claims, 15 Drawing Sheets
(6 of 15 Drawing Sheet(s) Filed in Color)

(56) References Cited

U.S. PATENT DOCUMENTS

2012/0128218 A1* 5/2012 Amyot et al. ............... 382/128
2012/0245465 A1* 9/2012 Hansegard et al. .......... 600/443
2013/0182926 A1* 7/2013 Lee ............................. 382/131
2014/0073925 A1* 3/2014 Kho et al. .................... 600/443

FOREIGN PATENT DOCUMENTS

KR 10-2010-0106633 A 10/2010
WO 89/05493 A1 6/1989

* cited by examiner

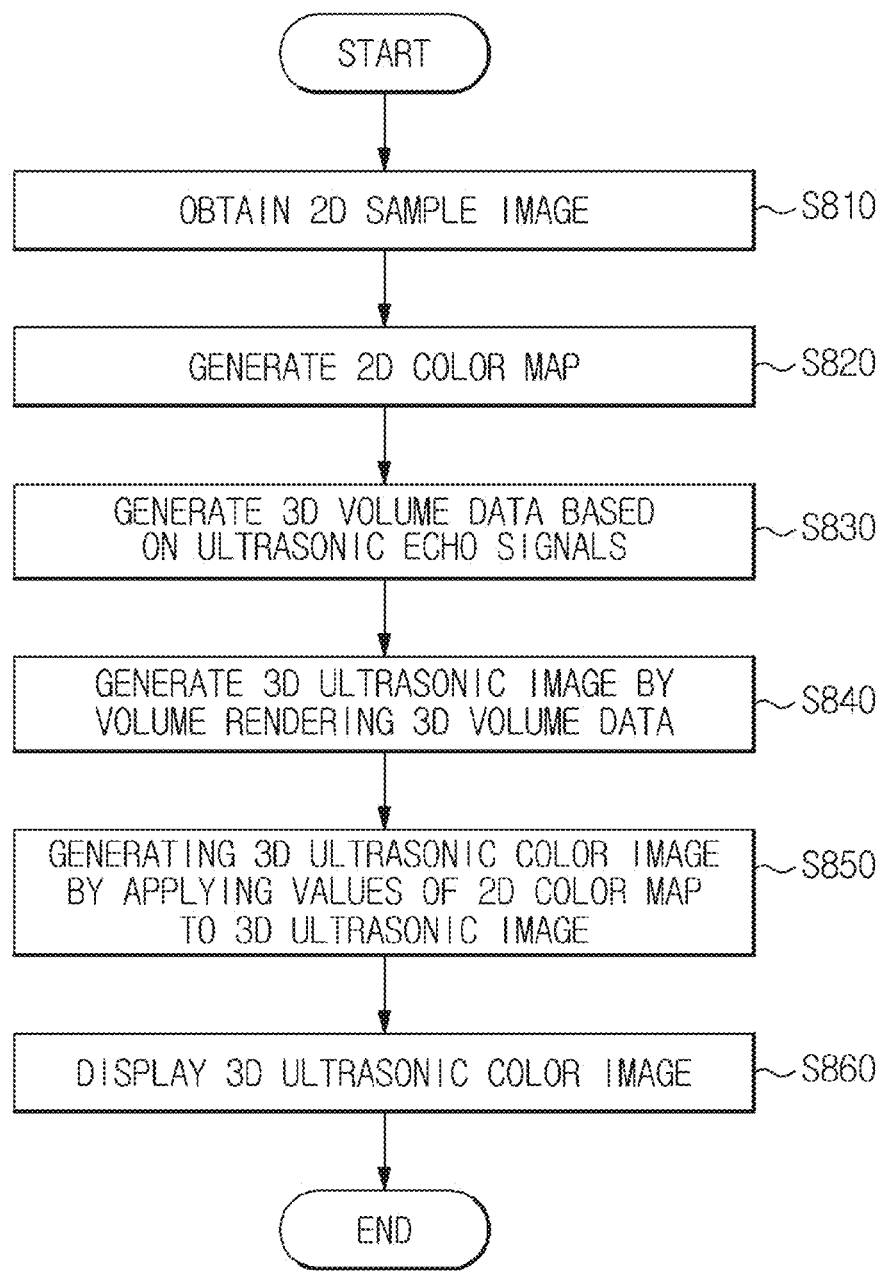

APPARATUS AND METHOD FOR GENERATING ULTRASONIC IMAGE

CROSS-REFERENCE TO RELATED APPLICATION

This application claims the priority from Korean Patent Application No. 10-2012-0100886, filed on Sep. 12, 2012 in the Korean Intellectual Property Office, the disclosure of which is incorporated herein by reference in its entirety.

BACKGROUND

1. Field

Methods and apparatuses consistent with exemplary embodiments relate to generating a three-dimensional (3D) ultrasonic color image of a fetus based on skin color of a mother.

2. Description of the Related Art

An ultrasonic diagnostic apparatus is an apparatus that irradiates an ultrasonic signal to a region of a body of an object and noninvasively acquires an image regarding soft tissue tomograms of blood flow by use of information obtained from a reflected ultrasonic signal (ultrasonic echo signal).

The ultrasonic diagnostic apparatus is small and inexpensive, executes display in real time and has high safety as there is no exposure to radiation, for example, x-rays, when compared to other image diagnosis apparatuses, such as an X-ray apparatus, a computed tomography (CT) scanner, a magnetic resonance imager (MRI), and a nuclear medicine apparatus. Thus, the ultrasonic diagnostic apparatus is widely used for heart diagnosis, breast diagnosis, celiac diagnosis, urinary diagnosis, and obstetrical diagnosis.

An ultrasonic diagnostic apparatus includes a body that accommodates main components of the ultrasonic diagnostic apparatus, a probe that transmits and receives ultrasonic waves, a control panel that includes various switches and keys to input a command to manipulate the ultrasonic diagnostic apparatus, and a display unit to display the results as an image.

A medical professional performs ultrasonic imaging by moving the probe on the surface of the object with one hand and manipulating the control pad with the other hand. An ultrasonic image is displayed on the display unit in real time. Accordingly, the medical professional may diagnose the condition of the object.

However, since the ultrasonic image obtained through ultrasonic diagnosis is a black-and-white image, realistic perception of the image is limited. In order to overcome such limitation, in the related art, a method of forming a 3D ultrasonic color image based on an arbitrarily selected color has been used. However, such the 3D ultrasonic color image is not sufficient since the color of the 3D ultrasonic color image is not based on true color of the imaged object. Particularly, a 3D ultrasonic image of a fetus is less realistic than 3D ultrasonic images of a heart or breast.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide an ultrasonic image generating apparatus capable of generating a 3D ultrasonic color image of a fetus based on skin color of a mother and a method of generating an ultrasonic image.

In accordance with an aspect of an exemplary embodiment, there is provided an apparatus for generating an ultrasonic image including a sample image acquisition unit acquiring one or more sample images by photographing skin of a pregnant woman, a two-dimensional (2D) color map generator generating a 2D color map based on the one or more sample images, a probe irradiating ultrasonic signals into the body of the pregnant woman and receiving reflected ultrasonic echo signals from a fetus therein, a volume data generator generating 3D volume data based on the ultrasonic echo signals, and a controller generating a 3D ultrasonic color image of the fetus by applying values of the 2D color map to a 3D ultrasonic image obtained by volume rendering of the 3D volume data.

The one or more sample images may be obtained by varying exposure time of the sample image acquisition unit.

The controller may control the exposure time of the sample image acquisition unit while performing ultrasonic diagnosis.

The apparatus may further include a lighting unit irradiating light toward skin of the pregnant woman, and the one or more sample images may be obtained by varying brightness of the lighting unit.

The controller may control brightness of the lighting unit while performing ultrasonic diagnosis.

The lighting unit may be disposed in the probe.

The sample image acquisition unit may be disposed in the probe.

The 2D color map generator may convert values of pixels constituting the one or more sample images into lightness (L*), chroma (C*), and hue (h) values, and generate the 2D color map by mapping the lightness (L*) and chroma (C*) along the horizontal axis and the hue (h) along the vertical axis.

The pixels of the 3D ultrasonic image may have shading values and depth values from a viewpoint, and the controller may generate the 3D ultrasonic color image by searching the horizontal axis and the vertical axis of the 2D color map for the shading values and the depth values and mapping the searched coordinate values to the pixels of the 3D ultrasonic image.

The apparatus may further include a display displaying the 3D ultrasonic color image.

In accordance with an aspect of an exemplary embodiment, there is provided a method of generating an ultrasonic image including acquiring one or more sample images by photographing skin of a pregnant woman using a sample image acquisition unit, generating a 2D color map based on the one or more sample images using a 2D color map generator, irradiating ultrasonic signals into the body of the pregnant woman and receiving reflected ultrasonic echo signals from a fetus therein using a probe, generating 3D volume data based on the ultrasonic echo signal using a volume data generator, and generating a 3D ultrasonic color image of the fetus by applying values of the 2D color map to a 3D ultrasonic image obtained by volume rendering of the 3D volume data.

The acquiring of one or more sample images may include acquiring one or more sample images having different brightness by adjusting exposure time of the sample image acquisition unit.

The acquiring of one or more sample images may include acquiring one or more sample images having different brightness by adjusting brightness of a lighting unit irradiating light to the skin of the pregnant woman.

The lighting unit may be disposed in the probe.

The sample image acquisition unit may be disposed in the probe.

The generating of a 2D color map may include converting values of pixels constituting the one or more sample images into lightness (L*), chroma (C*), and hue (h) values, and generating the 2D color map by mapping the lightness (L*) and chroma (C*) along the horizontal axis and the hue (h) along the vertical axis.

The pixels of the 3D ultrasonic image may have shading values and depth values from a viewpoint, and the generating of a 3D ultrasonic color image may include searching the horizontal axis and the vertical axis of the 2D color map for the shading values and the depth values, and mapping the searched coordinate values to the pixels of the 3D ultrasonic image.

The method may further include displaying the 3D ultrasonic color image on a display.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and/or other aspects will become more apparent by describing certain exemplary embodiments, with reference to the accompanying drawings, in which:

FIG. 12 is a flowchart illustrating a method of generating an ultrasonic image.

DETAILED DESCRIPTION

Figure 1:
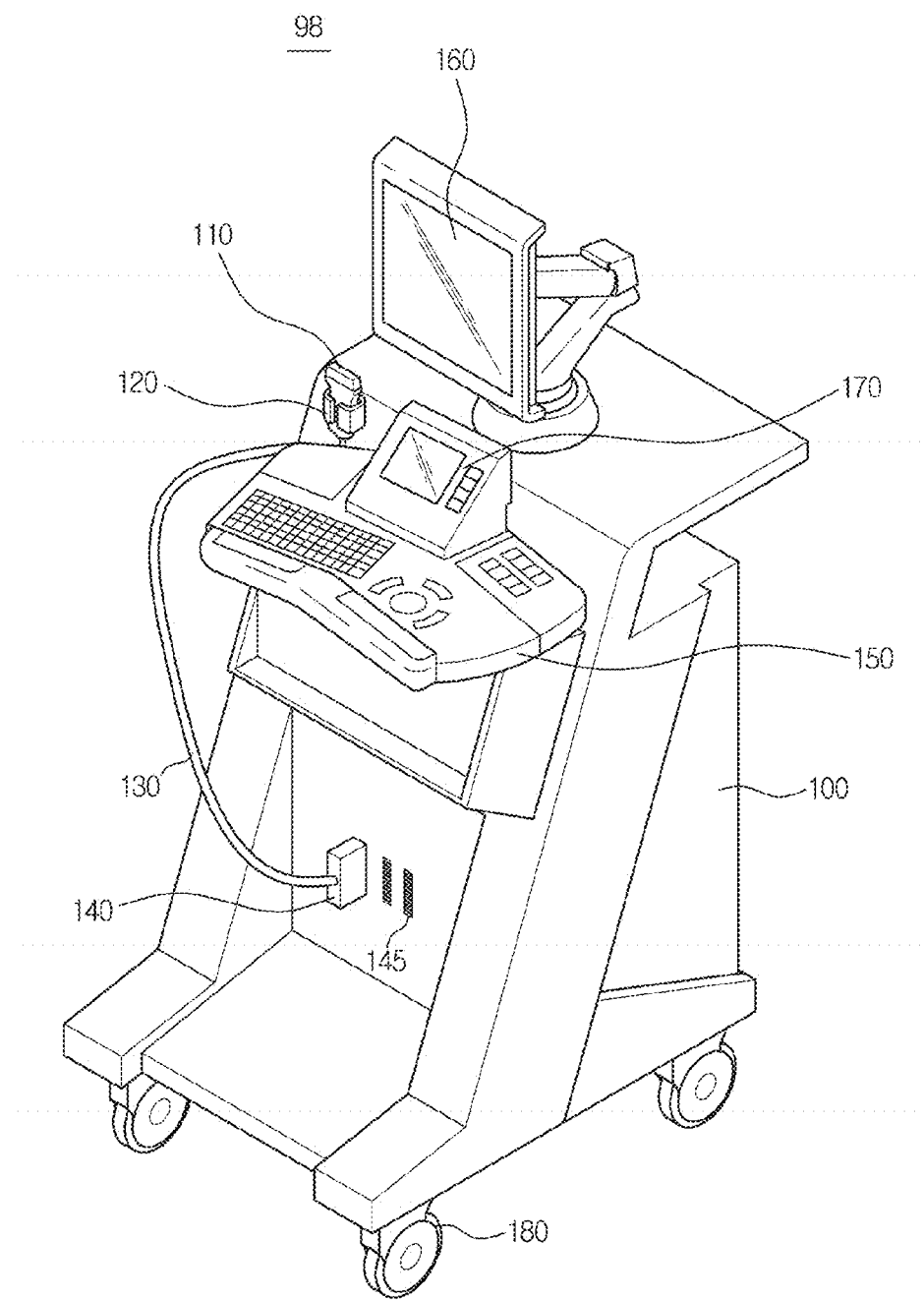
FIG. 1 is a perspective view illustrating an ultrasonic image generating apparatus according to an exemplary embodiment.

Certain exemplary embodiments are described in greater detail below with reference to the accompanying drawings. In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 is a perspective view illustrating an ultrasonic image generating apparatus according to an exemplary embodiment. As illustrated in FIG. 1, the ultrasonic image generating apparatus 98 may include a body 100, a probe 110, an input unit 150, a main display 160, and a sub display 170.

Figure 3:
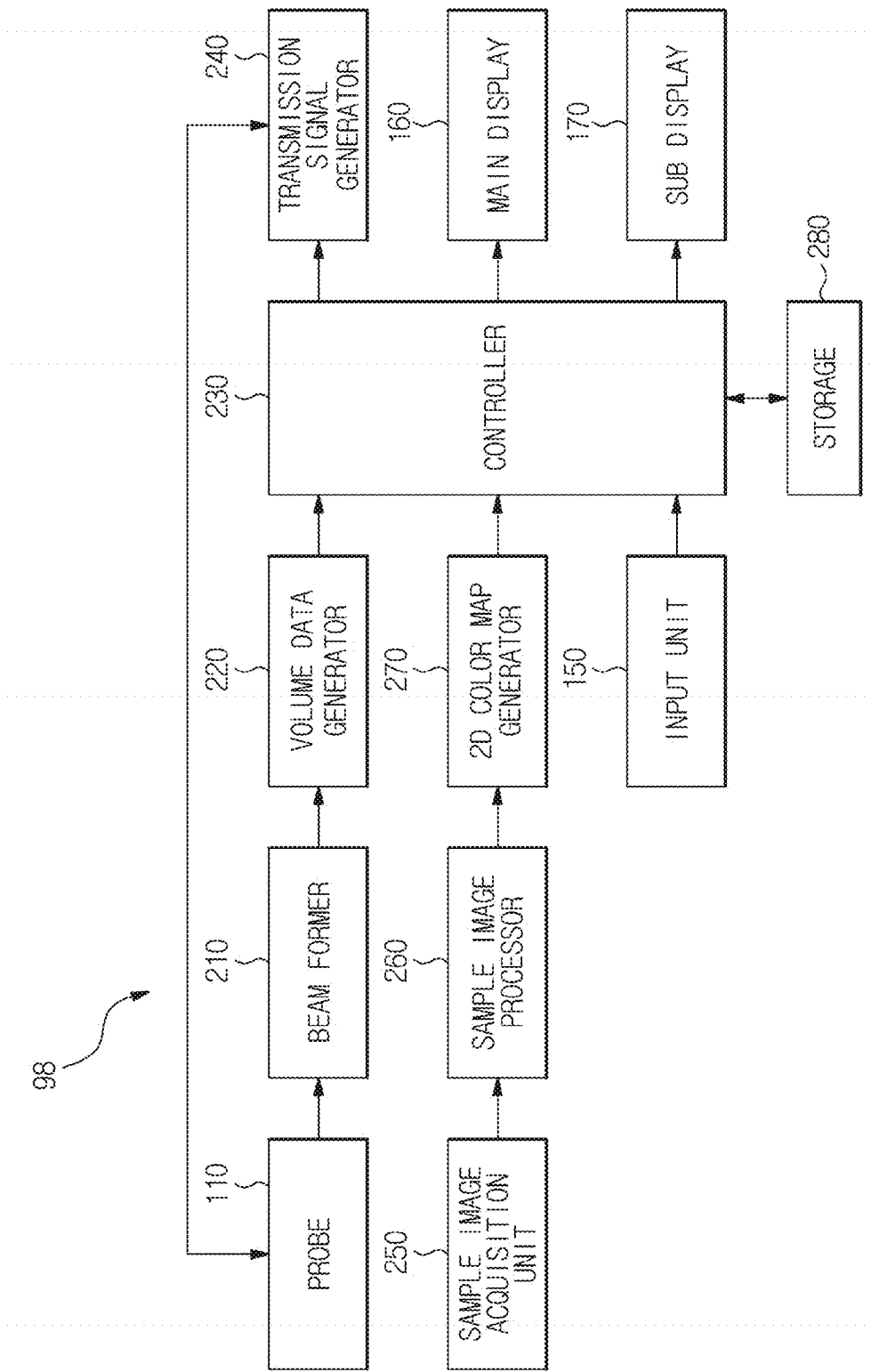
FIG. 3 is a block diagram illustrating a control configuration of an ultrasonic image generating apparatus according to an exemplary embodiment.

The body 100 of the ultrasonic image generating apparatus may accommodate various components, for example, a transmission signal generator 240 (FIG. 3). When a medical professional inputs a command to initiate ultrasonic imaging, the transmission signal generator 240 generates a transmission signal and transmits the signal to the probe 110.

The body 100 may be provided with at least one female connector 145 at one side. A male connector 140 connected to a cable 130 is physically connected to the female connector 145. The transmission signal generated by the transmission signal generator 240 is sent to the probe 110 via the male connector 140 connected to the female connector 145 of the body 100 and the cable 130.

Meanwhile, the body 100 may be provided with a plurality of casters 180 at a lower portion to facilitate movement of the ultrasonic image generating apparatus. The casters are used to fix the ultrasonic image generating apparatus at a predetermined position or to move the ultrasonic image generating apparatus in a predetermined direction.

The probe 110 that contacts the surface of an object, e.g., the abdomen of a pregnant woman, transmits and receives ultrasonic waves. Particularly, the probe 110 irradiates the transmission signal, i.e., ultrasonic signal, received from the body 100 to a target region, i.e., region of interest (ROI), in the body of the object, receives a reflected ultrasonic echo signal from the target region, e.g., a fetus, and transmits the ultrasonic echo signal to the body 100. One end of the cable 130 is connected to the probe 110, and the other end of the cable 130 is connected to the male connector 140. The male connector 140 connected to the other end of the cable 130 may be physically coupled to the female connector 145 of the body 100.

The input unit 150 receives a command associated with operation of the ultrasonic image generating apparatus. For example, the input unit 150 may receive a command to select a mode such as an amplitude mode (A-mode), a brightness mode (B-mode), and/or a motion mode (M-mode) or a command to initiate ultrasonic imaging. The command input through the input unit 150 may be transmitted to the body 100 via a wired or wireless communication system.

The input unit 150 may include at least one of a keyboard, a foot switch, and a foot pedal. The keyboard is implemented as hardware and is disposed at an upper portion of the body 100. The keyboard may include at least one of a switch, a key, a joystick, and a trackball. Alternatively, the keyboard may be implemented as software such as a graphical user interface. In this regard, the keyboard may be displayed on the sub display 170 or the main display 160. The foot switch or foot pedal may be disposed at a lower portion of the body 100. The user may control the operation of the ultrasonic image generating apparatus by use of the foot pedal.

A probe holder 120 to hold the probe 110 may be disposed around the input unit 150. At least one probe holder 120 may be provided. The user may place the probe 110 in the probe holder 120 while the ultrasonic image generating apparatus is not in use.

The sub display 170 may be provided at the body 100. FIG. 1 illustrates that the sub display 170 is disposed on the input unit 150. The sub display 170 may display applications associated with operation of the ultrasonic image generating apparatus. For example, the sub display 170 may display a menu or instructions required for ultrasonic diagnosis. The sub display 170 may include a cathode ray tube (CRT), a liquid crystal display (LCD), or the like.

The main display 160 may be provided at the body 100. FIG. 1 illustrates that the main display 160 is disposed higher than the sub display 170. The main display 160 may display an ultrasonic image obtained during the ultrasonic imaging. The main display 160 may include a CRT, an LCD, or the like in the same manner as the sub display 170. FIG. 1 illustrates that the main display 160 is coupled to the body 100. However, the main display 160 may be detachably disposed on the body 100.

In FIG. 1, the ultrasonic image generating apparatus is provided with both the main display 160 and the sub display 170. However, the sub display 170 may be omitted, and the applications or menus displayed on the sub display 170 may be displayed on the main display 160.

Figure 2A:
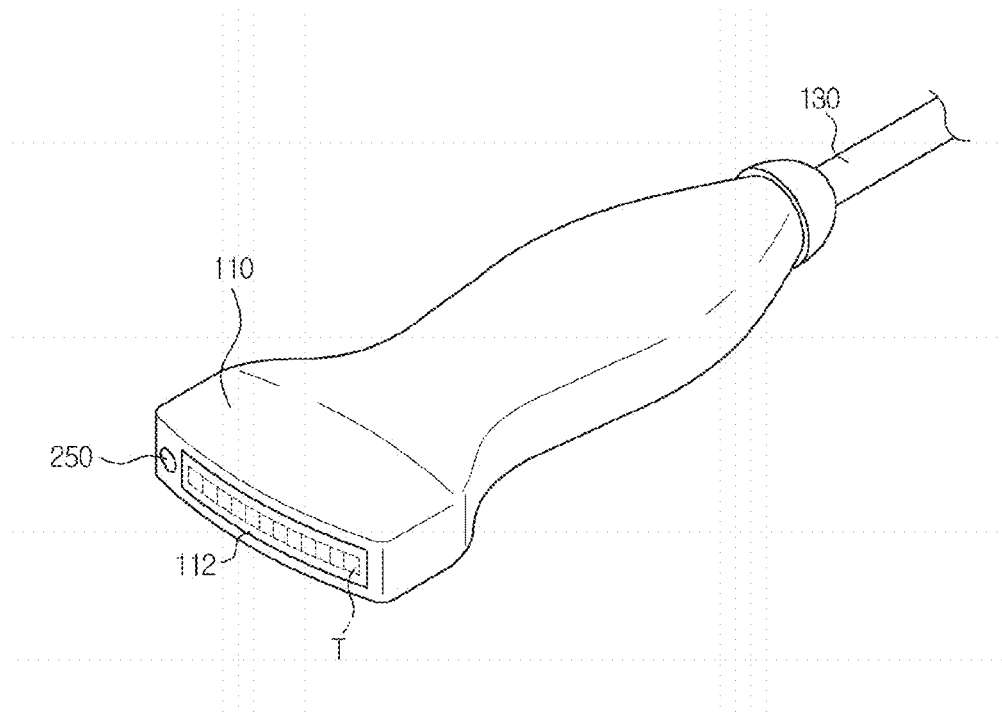
FIGS. 2A and 2B are perspective views illustrating probes.
Figure 2B:
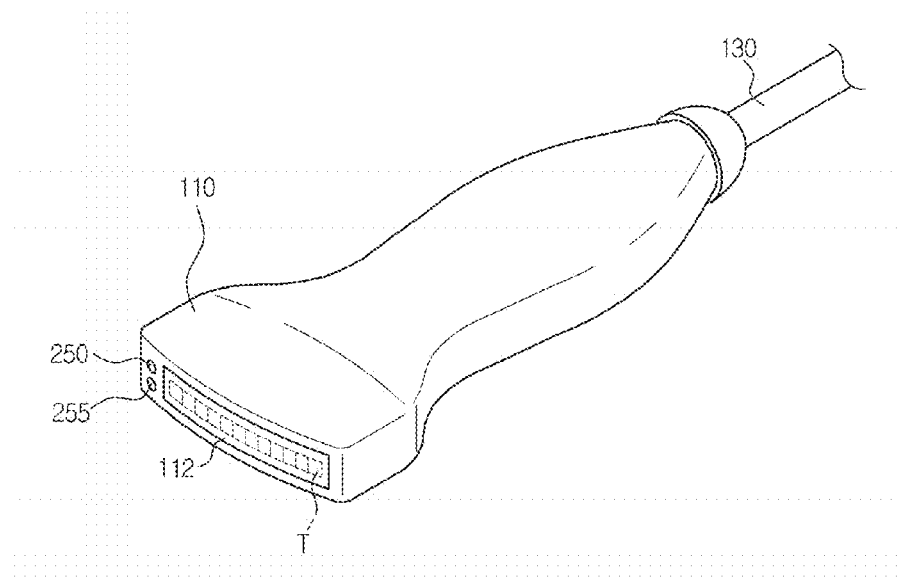

The probe will be described with reference to FIGS. 2A and 2B. FIG. 2A is a perspective view of a probe according to an exemplary embodiment. FIG. 2B is a perspective view of a probe according to another exemplary embodiment.

Referring to FIGS. 2A and 2B, a plurality of ultrasonic transducers T that generate ultrasonic waves in accordance with an electric signal and a sample image acquisition unit 250 may be provided at one end of the probe 110.

The ultrasonic transducers T may generate ultrasonic waves according to applied AC current. In particular, the ultrasonic transducers T may receive AC power from an external power supply device or an internal power storage device, for example, a battery. The piezoelectric vibrators, thin films, and the like contained in the ultrasonic transducers T may vibrate according to the supplied AC power, thereby generating ultrasonic waves.

A variety of ultrasonic transducers T such as magnetostrictive ultrasonic transducers using magnetostriction of a magnetic material, piezoelectric ultrasonic transducers using the piezoelectric effect of a piezoelectric material, or capacitive micromachined ultrasonic transducers (cMUT) transmitting and receiving ultrasonic waves using vibrations of hundreds or thousands of micro-processed thin films may be used.

The ultrasonic transducers T may be linear array transducers or convex array transducers. In FIGS. 2A and 2B, convex array ultrasonic transducers T are illustrated.

A cover 112 may be disposed on the ultrasonic transducers T to cover the ultrasonic transducers T.

The sample image acquisition unit 250 acquires one or more sample images with different brightness by photographing skin of an object, i.e., a pregnant woman. In this regard, the sample images may be images including information regarding skin color or skin texture of the pregnant woman.

For example, the sample image acquisition unit 250 may include a camera in which a lens, an image sensor, an infrared cut-off filter (IR filter), an actuator, and a flexible PCB (FPCB) are assembled. In this case, sample images with different brightness may be obtained by adjusting exposure time of the camera module. In this regard, the adjustment of the exposure time of the camera may be performed during ultrasonic imaging. In addition, a command to control the exposure time of the camera may be transmitted to a controller 230 (FIG. 3) provided at the body 100. FIG. 2A illustrates that the probe 110 includes the sample image acquisition unit 250.

Alternatively, the sample image acquisition unit 250 may be implemented using an image sensor alone. Examples of the image sensor may include complementary metal-oxide-semiconductor (CMOS) image sensors and charge-coupled device (CCD) image sensors.

The image sensor may include an external lens, a micro lens, a color filter array, a pixel array, an A/D converter that converts an analog signal received from the pixel array into a digital signal, and a digital signal processor that processes the digital signal output from the A/D converter. The CCD image sensor may include an external lens, a micro lens, a color filter array, and a pixel array. The CMOS image sensor may include an external lens, a micro lens, a color filter lens, an A/D converter, and a digital signal processor which are disposed on a single chip.

When the sample image acquisition unit 250 is implemented using the image sensor alone, the probe 110 may further include a lighting unit 255 to irradiate light toward skin of the pregnant woman. In this case, sample images with different brightness may be obtained by controlling brightness of the lighting unit 255. In this regard, control of the brightness of the lighting unit 255 may be performed during ultrasonic imaging. In addition, a command to control brightness of the lighting unit 255 may be transmitted from the controller 230. FIG. 2B illustrates that the probe 110 includes the lighting unit 255 separately disposed from the sample image acquisition unit 250.

In FIG. 2B, the sample image acquisition unit 250 and the lighting unit 255 are disposed at one end of the probe 110, but the disclosure is not limited thereto. Particularly, the sample image acquisition unit 250 and the lighting unit 255 may be disposed at any portion of the probe 110. The sample image acquisition unit 250 and the lighting unit 255 may be respectively disposed to face the surface of the object. In addition, the sample image acquisition unit 250 and the lighting unit 255 may be disposed to be close to each other or to be spaced apart from each other. For example, the sample image acquisition unit 250 may be disposed at one end of the probe 110, and the lighting unit 255 may be disposed at a side of the probe 110.

The ultrasonic image generating apparatus according to an exemplary embodiment has been described so far. Hereinafter, control configuration and functions of components of the ultrasonic image generating apparatus will be described in more detail with reference to FIGS. 3 to 11.

FIG. 3 is a block diagram illustrating a control configuration of an ultrasonic image generating apparatus according to an exemplary embodiment.

As illustrated in FIG. 3, the ultrasonic image generating apparatus 98 may include a transmission signal generator 240, a probe 110, a beam former 210, a volume data generator 220, a sample image acquisition unit 250, a sample image processor 260, a 2D color map generator 270, a controller 230, an input unit 150, a storage 280, a main display 160, and a sub display 170.

The input unit 150, the main display 160, the sub display 170, and the sample image acquisition unit 250 are described above with reference to FIGS. 1, 2A and 2B, and thus a detailed description thereof will not be repeated.

By photographing skin of an object, i.e., a pregnant woman, the sample image acquisition unit 250 may acquire one or more sample images containing information regarding skin of the pregnant woman. In this regard, the sample images may have different brightness. In order to obtain sample images with different brightness, exposure time of the sample image acquisition unit 250 may be controlled, or brightness of a lighting unit 255 separately disposed from the sample image acquisition unit 250 may be controlled.

Figure 4:
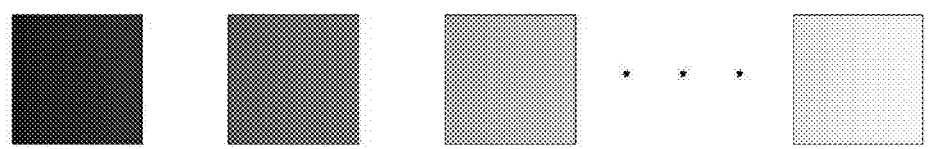
FIG. 4 is a diagram illustrating sample images obtained by photographing skin of a pregnant woman.

FIG. 4 illustrates sample images obtained from the sample image acquisition unit 250.

The sample image processor 260 may perform image processing of the sample images. For example, the sample image processor 260 may remove noise contained in the sample images by filtering the sample images. FIG. 3 illustrates that the ultrasonic image generating apparatus includes the sample image processor 260. However, the sample image processor 260 may be omitted.

The 2D color map generator 270 may generate a 2D color map based on the sample images. In this regard, the 2D color map refers to a lookup table in which colors used to form a 3D ultrasonic color image are listed in a 2D manner. A process of generating the 2D color map will be described in detail.

First, the 2D color map generator 270 may convert a color space of a sample image into a uniform color space. Particularly, a sample image acquired by the sample image acquisition unit 250 may be a color image expressed in the RGB color space. This indicates that each pixel of the sample image is represented by RGB values. However, since the RGB color space is not a uniform color space, the color space may be converted into a uniform color space, for example, the CIE LCH color space in order to obtain significant information from the sample image.

The CIE LCH color space is one of the standards set by the International Commission on Illumination (CIE) using cylindrical coordinates. The CIE LCH color space is represented by L*, C*, and h. In this regard, L* refers to lightness with a value range of 0 (black) to 100 (white). C* refers to chroma represented as a distance from the center of a sphere. H refers to hue represented by an angle from 0 to 360 degrees, where red is 0, yellow is 90 degrees, green is 180 degrees, blue is 270 degrees, and 360 degrees, i.e., 0, is red.

Conversion of the color space of the sample image from the RGB color space into the CIE LCH color space refers to a conversion of R, G, and B values of each pixel of the sample image into L*, C*, and h values. The conversion from the RGB color space into the CIE LCH color space is known to those skilled in the art, and thus a detailed description thereof will not be given here.

After completion of the conversion of the color space, the 2D color map generator 270 may generate a 2D color map by two-dimensionally arranging the converted values. That is, among the converted values, the 2D color map generator 270 may map lightness (L*) and chroma (C*) onto the horizontal axis and hue (h) onto the vertical axis.

Figure 5:
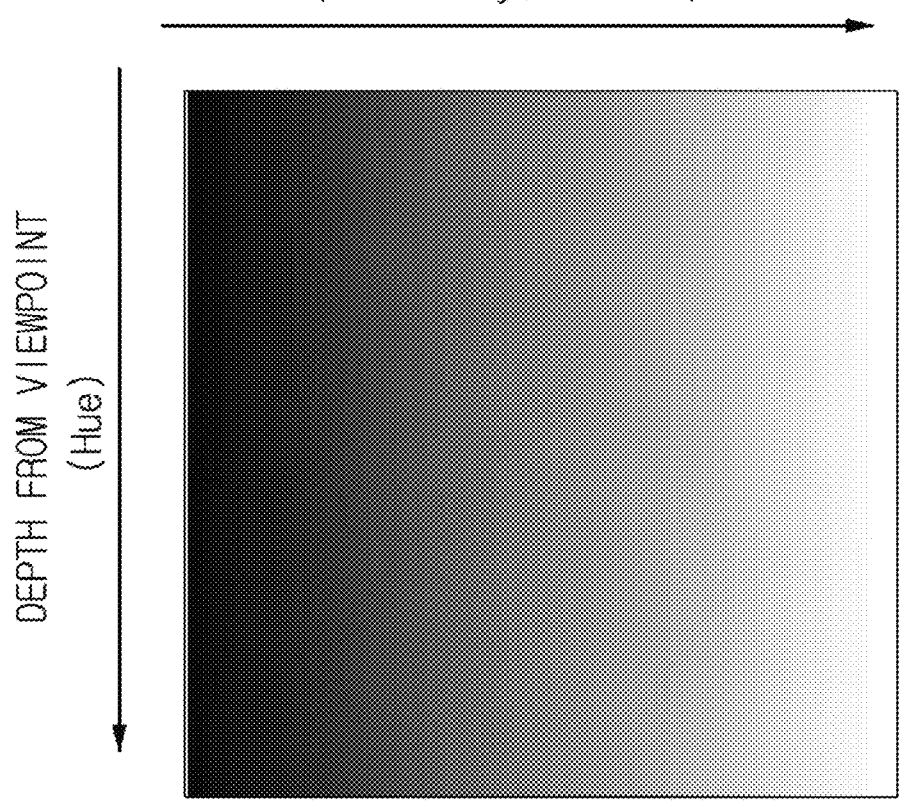
FIG. 5 is a 2D color map generated based on one or more sample images.

As a result, a 2D color map as illustrated in FIG. 5 may be generated. Here, lightness may also be replaced with a term luminance or intensity. Intensity and chroma values are mapped onto the horizontal axis of the 2D color map shown in FIG. 5. The horizontal axis of the 2D color map generated according to such method may correspond to a shading value of a 3D ultrasonic image obtained through volume rendering of volume data. In addition, the vertical axis of the 2D color map may correspond to a depth value of the 3D ultrasonic image.

Meanwhile, after completion of mapping of the lightness, chroma, and hue, the 2D color map generator 270 may convert lightness, chroma, and hue values allocated to each coordinates of the 2D color map into R, G, and B values.

Referring back to FIG. 3, the transmission signal generator 240 may generate transmission signals in consideration of the positions of the ultrasonic transducers T and the focusing point. In this regard, the transmission signals refer to high-voltage electric signals to vibrate the ultrasonic transducers T. The generated transmission signals are transmitted to the ultrasonic transducers T of the probe 110.

The ultrasonic transducers T of the probe 110 may convert the transmission signals into ultrasonic signals, irradiate the ultrasonic signals to an object, and receive ultrasonic echo signals from the object. The received ultrasonic echo signals may be transmitted to the beam former 210.

The beam former 210 may convert the analog ultrasonic echo signals into digital signals. In addition, the beam former 210 applies a time delay to the digital signals taking into consideration the locations of the ultrasonic transducers T and the focusing point and generates a receive focus signal. The receive focus signal generated by the beam former 210 may be interpreted as a cross-sectional image.

Figure 6:
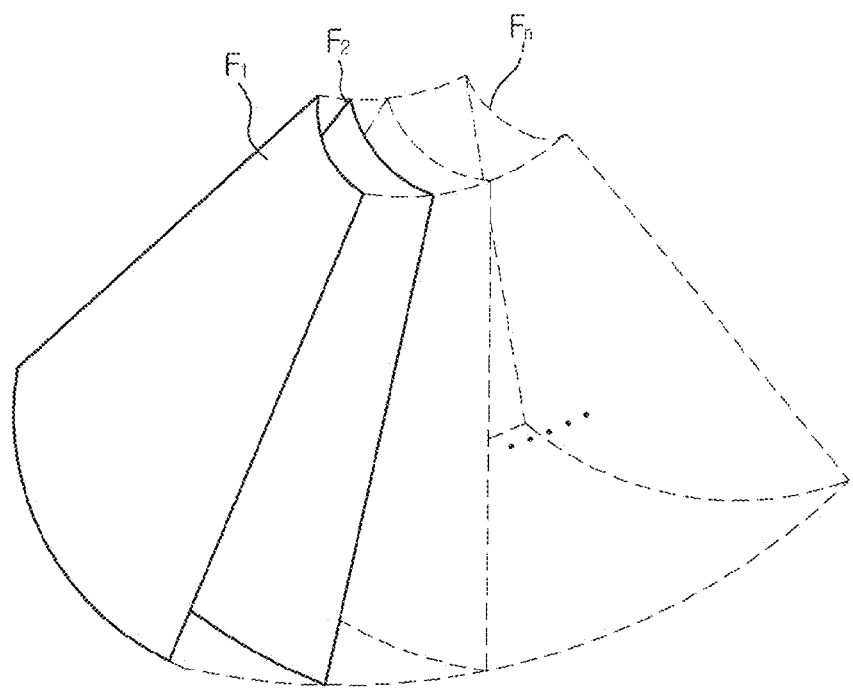
FIG. 6 is a diagram illustrating a plurality of cross-sectional images.

A plurality of cross-sectional images $F_1$ and $F_2$ to $F_n$ may be generated as shown in FIG. 6.

Figure 7:
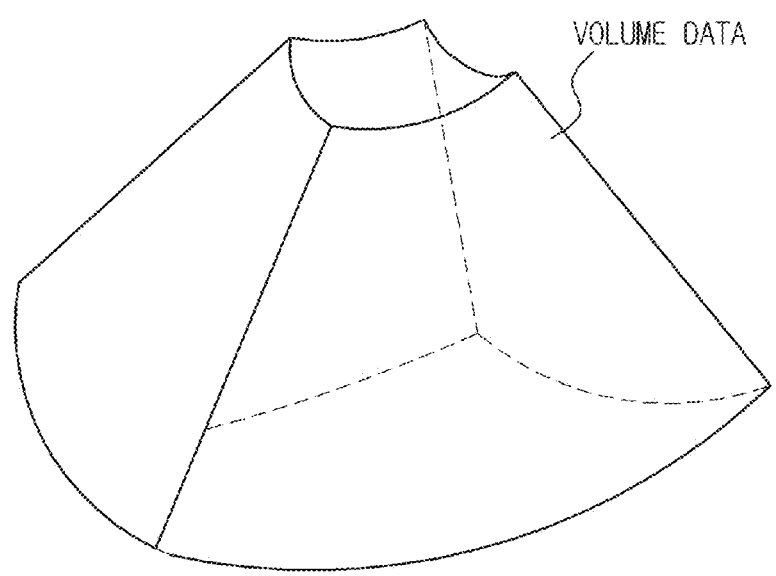
FIG. 7 is a diagram illustrating volume data.

The volume data generator 220 may produce 3D volume data of the object based on the plurality of cross-sectional images generated by the beam former 210 as illustrated in FIG. 7. The volume data may be represented by a plurality of voxels. While a pixel defines a point in a 2D space, a voxel defines a point in a 3D space. While the pixel includes x and y coordinates, the voxel includes x, y, and z coordinates.

Referring back to FIG. 3, the controller 230 may generate a 3D ultrasonic image by volume-rendering of 3D volume data. That is, the controller 230 may generate a 2D projected image of the 3D volume data.

The controller 230 may perform volume rendering of 3D volume data by surface rendering and/or direct volume rendering.

The surface rendering is a technique including extracting surface information from volume data based on uniform scalar values and spatial variation, converting the surface information into geometric elements such as polygons or surface patches, and applying a conventional rendering method thereto. Examples of the surface rendering may include a marching cube algorithm and dividing cube algorithm.

Direct volume rendering is a technique of directly rending volume data without converting the volume data into geometric elements. The direct volume rendering may directly visualize internal information of an object and may be efficiently used to represent a semitransparent structure. The direct volume rendering may be classified into object-order method and image-order method according to ways of approaching to the volume data.

The image-order method is a method of sequentially determining pixel values of an image. Ray-casting is an image-order method. Here, ray-casting will be briefly described with reference to FIG. 8.

Figure 8:
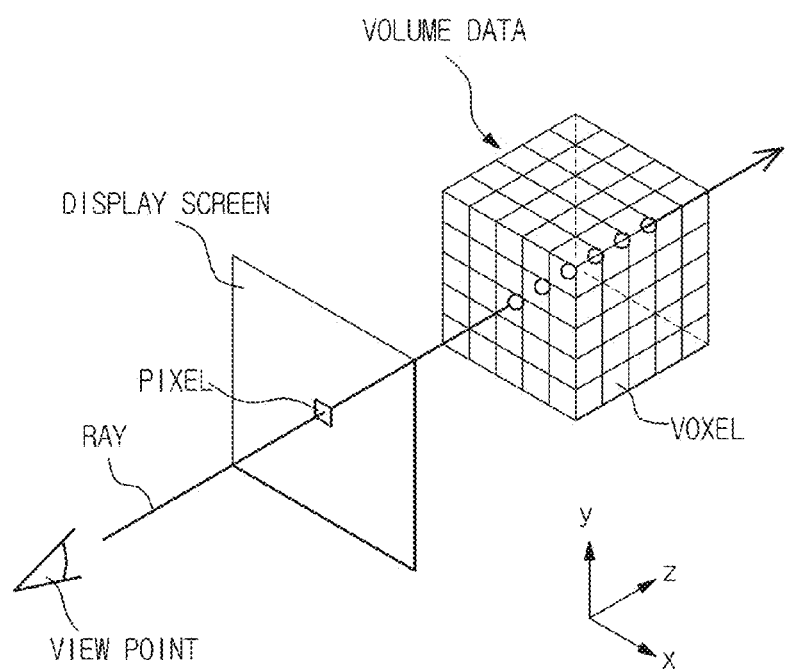
FIG. 8 is a diagram for describing volume rendering.

According to ray-casting as illustrated in FIG. 8, virtual rays are cast from a viewpoint toward a specific pixel of a display screen, and voxels through which the ray passes are detected among voxels of volume data. Then, brightness values of detected voxels are accumulated to determine brightness or transparency of the pixel. Alternatively, an average of the detected voxels may be determined as a brightness of the pixel, or a weighted average of the detected voxels may be determined as a brightness of the pixel.

In addition to the above-mentioned volume rendering, the controller 230 may also use ray-tracing. Here, ray-tracing refers to a technique of tracing the path of rays reaching eyes of an observer.

Meanwhile, the controller 230 may further perform shading, hidden surface processing, and the like during volume rendering. Here, shading refers to a process of imparting a sense of depth by varying levels of darkness when displaying a 3D object on a 2D screen. That is, a portion farther from the viewpoint is displayed darker, and a portion closer to the viewpoint is displayed brighter. Hidden surface processing refers to a process of removing portions that are hidden from the viewpoint and displaying visible portions on a 2D screen. Such processes may be performed to compensate for data loss caused by a 3D dimensional to 2D dimensional reduction and to obtain images with a natural appearance.

Figure 9:
FIG. 9 is a 3D ultrasonic image generated by volume rendering.

After completion of volume rendering, a 3D ultrasonic image as illustrated in FIG. 9 may be generated. In this regard, each pixel of the 3D ultrasonic image may have a shading value and a depth value from the view point.

When the 3D ultrasonic image is generated through volume rendering, the controller 230 may generate a 3D ultrasonic color image of a fetus by applying values of the 2D color map to each pixel of the 3D ultrasonic image. In this regard, the values of the 2D color map applied to the 3D ultrasonic image may be determined based on the shading value and the depth value of each pixel of the 3D ultrasonic image.

Figure 10:
FIG. 10 is a 3D ultrasonic color image generated by applying values of a 2D color map to a 3D ultrasonic image.

Particularly, the controller 230 may apply coordinate values of the 2D color map to the corresponding pixel. The coordinate values include a coordinate value of a point corresponding to the shading value of the pixel in the horizontal axis of the 2D color map and a coordinate value of a point corresponding to the depth value of the pixel in the vertical axis of the 2D color map. The controller 230 may respectively apply values of the 2D color map to all of the pixels of the 3D ultrasonic image to generate a 3D ultrasonic color image as illustrated in FIG. 10.

Referring back to FIG. 3, the storage 280 may store data or algorithms used to operate the ultrasonic image generating apparatus. For example, the storage 280 may store algorithms to convert the color space of a sample image, algorithms to generate a 2D color map based on one or more sample images, algorithms to generate volume data based on a plurality of cross-sectional images, algorithms to render volume data, algorithms to generate a 3D ultrasonic color image, a 2D color map generated in the 2D color map generator 270, a shading value and a depth value of each pixel of a 3D ultrasonic image, and the like.

The storage 280 may be implemented as a nonvolatile memory device such as a read only memory (ROM), programmable read only memory (PROM), erasable programmable read only memory (EPROM) and a flash memory, or a volatile memory device such as random access memory (RAM), or a storage medium such as hard disk or optical disc. However, the storage 280 is not limited to these examples and may be implemented by any other devices.

Figure 11A:
FIGS. 11A, 11B, and FIG. 11C illustrate 3D ultrasonic color images of a fetus represented by different shades of the skin color of a mother.
Figure 11B:
Figure 11C:

FIG. 11A to FIG. 11C illustrate 3D ultrasonic color images illustrating a fetus according to skin color of a mother.

FIG. 11A illustrates a 3D ultrasonic color image of a fetus of a pregnant woman whose skin color is dark (e.g., black) obtained by ultrasonic imaging. FIG. 11B illustrates a 3D ultrasonic color image of a fetus of a pregnant woman having skin color which is lighter than illustrated in FIG. 11A obtained by ultrasonic imaging. FIG. 11C illustrates a 3D ultrasonic color image of a fetus of a pregnant woman having skin color which lighter than illustrated in FIG. 11B (e.g., white) obtained by ultrasonic imaging.

Referring to FIGS. 11A, 11B, and 11C, skin color of the fetus in each of the 3D ultrasonic color images varies in accordance with the skin color of the mother. When skin color of the fetus is depicted based on skin color of the mother during generation of a 3D ultrasonic color image of the fetus, as described above, psychological satisfaction and emotional security of the mother and family may be improved in comparison with depiction of skin color of the fetus based on arbitrarily selected color.

FIG. 12 is a flowchart illustrating a method of generating an ultrasonic image.

When ultrasonic imaging is initiated, a user moves the probe 110 while maintaining contact with the abdomen of a pregnant woman. During ultrasonic imaging, the sample image acquisition unit 250 of the probe 110 photographs skin of the pregnant woman to obtain one or more 2D sample images (S810). In this regard, the 2D sample images may have different brightness. 2D sample images having different brightness may be obtained by adjusting exposure time of the sample image acquisition unit 250 or adjusting brightness of the lighting unit 255 separately disposed from the sample image acquisition unit 250.

When the 2D sample images are acquired, a 2D color map may be generated based on the acquired 2D sample images (S820). The generating of the 2D color map may include converting RGB values of a pixel constituting the sample image into lightness, chroma, and hue values, generating a 2D color map by mapping the lightness and chroma values, among the converted value, along the horizontal axis, and mapping the hue values along the vertical axis, and converting the lightness, chroma and hue values allocated to each of the coordinates of the 2D color map into R, G, and B values.

Meanwhile, when ultrasonic imaging is initiated, ultrasonic signals are irradiated from the probe 110 to the abdomen of the pregnant woman, and ultrasonic echo signals reflected by the object (fetus) of the abdomen are received by the probe 110. Then, 3D volume data may be generated based on the received ultrasonic echo signals (S830). Generating the 3D volume data may include converting the analog ultrasonic echo signals into digital signals, generating a plurality of receive focus signals by receiving and focusing the digital signals, and generating 3D volume data of the object (fetus) based on the plurality of receive focus signals.

When the 3D volume data is generated, the 3D volume data is rendered to generate a 3D ultrasonic image (S840). In this operation, surface rendering or direct volume rendering may be used as volume rendering. In addition, the 3D ultrasonic image generated by volume rendering may be regarded as a 2D projected image of the 3D volume data. Each of the 3D ultrasonic image may have a shading value and a depth value from a viewpoint.

When the 3D ultrasonic image is generated by volume rendering, a 3D ultrasonic color image of the fetus may be generated by applying the values of the 2D color map to the generated 3D ultrasonic image (S850). The generating of the 3D ultrasonic color image (S850) may include searching the horizontal axis and the vertical axis of the 2D color map for shading values and depth values of pixels of the 3D ultrasonic image, and mapping values corresponding to the searched coordinates to pixels of the 3D ultrasonic image.

The generated 3D ultrasonic color image may be displayed on the main display (S860). In this regard, the main display may be mounted on the ultrasonic image generating apparatus or separately disposed from the ultrasonic image generating apparatus at a remote location to communicate with the ultrasonic image generating apparatus in a wired or wireless manner.

Exemplary embodiments may be implemented by media including computer-readable code/commands to control at least one processing element, for example, computer-readable media. The media may correspond to a medium/media enabling storage and/or transmittance of computer-readable code.

The computer-readable code may be recorded in media or transmitted via the Internet. Examples of the media include recording media such as magnetic storage media (for example, ROM, floppy disk, hard disk or the like) and optical recording media (for example, CD-ROM or DVD) and transmission media such as carrier waves. Also, in exemplary embodiments, the media may be signals such as composite signals or bitstreams. The media may be a distributed network and computer-readable code may be stored and/or transmitted and executed in a distributed manner. Furthermore, in one example, the processing element includes a processor or a computer processor and the processing element may be dispersed and/or included in one device.

According to exemplary embodiments, skin color of the fetus is depicted based on skin color of the mother during generation of a 3D ultrasonic color image of the fetus, so that psychological satisfaction and emotional security of the mother and family may be improved.

Since the sample image acquisition unit of the probe acquires sample images during ultrasonic diagnosis, the sample images may be obtained without causing unpleasant feelings to the mother.

Although a few exemplary embodiments have been shown and described, exemplary embodiments are not limited thereto. It would be appreciated by those skilled in the art that changes may be made in these exemplary embodiments without departing from the principles and spirit of the disclosure, the scope of which is defined in the claims and their equivalents.

What is claimed is:

1. An apparatus for generating an ultrasonic image, the apparatus comprising:
   a sample image acquisition unit configured to acquire a sample image by photographing a portion of a skin of a pregnant woman;
   a probe configured to irradiate ultrasonic signals toward a fetus of the pregnant woman and receives reflected ultrasonic echo signals;
   a processor configured to generate a 2D color map based on the sample image, generate three-dimensional (3D) volume data based on the ultrasonic echo signals, and generate a 3D ultrasonic color image of the fetus by applying values of the 2D color map to a 3D ultrasonic image obtained by volume rendering of the 3D volume data.

2. The apparatus according to claim 1, wherein the sample image is obtained by varying exposure time of the sample image acquisition unit.

3. The apparatus according to claim 2, wherein the processor is configured to control the exposure time of the sample image acquisition unit while performing ultrasonic imaging.

4. The apparatus according to claim 1, further comprising:
   a lighting unit configured to irradiate light toward the skin of the pregnant woman,
   wherein a plurality of sample images is obtained by varying brightness of the lighting unit.

5. The apparatus according to claim 4, wherein the processor is configured to control the brightness of the lighting unit while performing ultrasonic imaging.

6. The apparatus according to claim 1, wherein the processor is configured to convert values of pixels of the sample image into lightness (L*), chroma (C*), and hue (h) values, and generates the 2D color map by mapping the lightness (L*) and chroma (C*) along a horizontal axis and the hue (h) along a vertical axis.

7. The apparatus according to claim 6, wherein:
   the pixels of the 3D ultrasonic image have shading values and depth values from a viewpoint; and
   the processor is configured to generate the 3D ultrasonic color image by searching the horizontal axis and the vertical axis of the 2D color map for the shading values and the depth values and mapping the searched coordinate values to the pixels of the 3D ultrasonic image.

8. The apparatus according to claim 1, further comprising a display configured to display the 3D ultrasonic color image.

9. The apparatus of claim 1, wherein the sample image acquisition unit includes a camera configured to capture sample images of the portion of the skin with different brightness levels, by changing exposure durations of the camera, respectively, and
   the processor is configured to control a sample capturing operation, which is performed by the camera, by changing the exposure durations during ultrasonic imaging.

10. The apparatus of claim 1, wherein the probe includes:
   an end surface which contacts the skin during ultrasonic imaging; and
   ultrasonic transducers disposed on the end surface,
   wherein the sample image acquisition unit is disposed on the end surface of the probe, among the transducers.

11. A method of generating an ultrasonic image, the method comprising:
   acquiring a sample image by photographing a portion of a skin of a pregnant woman, with a sample image acquisition unit of an ultrasound apparatus;
   generating a two-dimensional (2D) color map based on the sample image;
   irradiating ultrasonic signals toward a fetus of the pregnant woman and receiving reflected ultrasonic echo signals, with an ultrasonic probe of the ultrasound apparatus;
   generating three-dimensional (3D) volume data based on the ultrasonic echo signals; and
   generating a 3D ultrasonic color image of the fetus by applying values of the 2D color map to a 3D ultrasonic image obtained by volume rendering of the 3D volume data.

12. The method according to claim 11, wherein the acquiring the sample image comprises acquiring a plurality of sample images having different brightness values by adjusting exposure time of the sample image acquisition unit.

13. The method according to claim 11, wherein the acquiring sample image comprises acquiring a plurality of sample images having different brightness values by adjusting brightness of a lighting unit which irradiates light to the skin of the pregnant woman.

14. The method according to claim 13, wherein the lighting unit is disposed in the ultrasonic probe.

15. The method according to claim 11, wherein the sample image acquisition unit is disposed in the ultrasonic probe.

16. The method according to claim 11, wherein the generating the 2D color map comprises:

converting values of pixels of the sample image into lightness (L*), chroma (C*), and hue (h) values; and generating the 2D color map by mapping the lightness (L*) and chroma (C*) along a horizontal axis and the hue (h) along a vertical axis.

17. The method according to claim 16, wherein:

the pixels of the 3D ultrasonic image have shading values and depth values from a viewpoint; and the generating the 3D ultrasonic color image comprises searching the horizontal axis and the vertical axis of the 2D color map for the shading values and the depth values, and mapping the searched coordinate values to the pixels of the 3D ultrasonic image.

18. The method according to claim 11, further comprising displaying the 3D ultrasonic color image on a display.

19. An apparatus comprising:

a probe configured to be in contact with a skin of a patient, to irradiate ultrasonic signals toward a region of interest (ROI) of the patient and receive reflected ultrasonic echo signals;

an imager disposed proximate the probe and configured to acquire a skin image of a portion of a skin of the patient during ultrasonic imaging;

a processor configured to generate a two-dimensional (2D) color map which stores pixel values of the skin image, generate three-dimensional (3D) volume data based on the ultrasonic echo signals, apply values of the 2D color map to a 3D ultrasonic image obtained from the 3D volume data, and generate a 3D ultrasonic color image of the ROI; and a display configured to display the 3D ultrasonic color image.

20. The apparatus according to claim 19, wherein the processor is further configured to vary an exposure time of the imager, and the imager is configured to acquire a plurality of skin images corresponding to different exposure times.

21. The apparatus according to claim 19, wherein the probe is configured to comprise a light source which illuminates the skin of the patient.

22. The apparatus according to claim 19, wherein the ROI comprises a fetus, the display is configured to display the 3D ultrasonic color image of the fetus, and color of the fetus in the 3D ultrasonic color image corresponds to a color of the skin of the patient.

* * * * *